United States Patent [19]

Hahnenberger

[11] Patent Number: 5,679,713
[45] Date of Patent: Oct. 21, 1997

[54] PHARMACEUTICAL COMPOSITION CONTAINING CARBACHOL AND OTHER CHOLINERGIC SUBSTANCES

[75] Inventor: Rudolph Wolfgang Hahnenberger, Uppsala, Sweden

[73] Assignee: Astra Aktiebolag, Sodertalje, Sweden

[21] Appl. No.: 326,797

[22] Filed: Oct. 20, 1994

Related U.S. Application Data

[63] Continuation of Ser. No. 927,831, Aug. 10, 1992, abandoned.

[30] Foreign Application Priority Data

Aug. 13, 1991 [SE] Sweden ................................. 9102340

[51] Int. Cl.$^6$ ................................................. A61K 31/14
[52] U.S. Cl. ................................. 514/642; 514/912
[58] Field of Search .......................... 514/642, 912

[56] References Cited

U.S. PATENT DOCUMENTS

| | | | |
|---|---|---|---|
| 2,185,220 | 1/1940 | Nabenhauer | 167/65 |
| 4,804,539 | 2/1989 | Guo et al. | 424/450 |

FOREIGN PATENT DOCUMENTS

| | | |
|---|---|---|
| 8800824 | 2/1988 | European Pat. Off. |
| 1386864 | 3/1975 | United Kingdom |

OTHER PUBLICATIONS

The Merck Index, Eleventh Edition, 1984, p. 268.

Victor F. Smolen et al., "Biophasic Availability of Ophthalmic Cabachol I: Mechanisms of Cationic Polymer–and Surfactant–Promoted Miotic Activity", J. Pharm. Sciences 62, 1973 (958–61).

Verinder S. Nirankari et al., "Ocular Manifestations of Shy–Drager Syndrome", Ann. Ophthalmol. (USA), 1982, 14/7 (635–38).

Han H. Stolze et al., "Influence of secretagogues on volume and protein pattern in rabbit lacrimal fluid", Curr Eye Res, (1985 Apr.) 4(4) 489–92.

"Dorland's Illustrated Medical Dictionary, 26th Ed.", 1985, W.B. Saunders Company, see p. 110 arecoline and see p. 217 carbachol.

Susan Budavari et al. "The Merck Index, eleventh edition", 1989, Merck & Co., Inc., USA, see p. 935 No. 5847, Methanol Chloride and see p. 185 No. 1207, Bethanechol Chloride.

Goodman and Gilman's "The Pharmacological Basis of Therapeutics" (Eighth's Ed) Chap. 6, pp. 126–127.

Meyler's Side Effects of Drugs Eleventh Ed. (Mng Dukes, ed) Elsevier 1988, Ch. 49, p. 991.

Primary Examiner—Zohreh Fay
Attorney, Agent, or Firm—White & Case

[57] ABSTRACT

The present invention relates to the use of carbachol and other cholinergic substances for the treatment of keratoconjunctivitis sicca.

10 Claims, No Drawings

PHARMACEUTICAL COMPOSITION CONTAINING CARBACHOL AND OTHER CHOLINERGIC SUBSTANCES

This application is a continuation of application Ser. No. 07/927,831 filed Aug. 10, 1992 now abandoned.

FIELD OF THE INVENTION

The present invention relates to the use of carbacholin as an active agent in pharmaceutical compositions for the treatment of keratoconjunctivitis sicca (dry eyes). The invention specifically concerns such use in eyedrops having the ability to stimulate natural tear production.

BACKGROUND ART

Dry eyes (keratoconjunctivitis sicca, KCS) is a disease characterised in reduced secretion of tears. Cornea and conjunctiva suffer from an inferior function of tear supply resulting in structural changes as epithelial cell death, corneal infiltrations and others. Patients are afflicted with smarting pain, sensations of dust, occasionally reduced vision, aches, irritation and so on. In its classical form KCS appears as Sjögren's syndrom involving engagement of other serous glands but KCS is much more common in its less serious form. It has been estimated that about 25% of the patients in an eye clinic suffer from more or less chronically dry eyes (Scharf, J., Zonis, S., Perelman J. and Hit, E., Harefuah., 1975, 89, p 505).

Treatment of dry eyes is today a major problem in ophtalmology. So far tear substitutions have mostly been offered to patients. Tear substitutions normally consist of salt solutions with a lubricant e.g. methyl cellulose, polyvinyl alcohol and hyaluronic acid. One important disadvantage of this treatment is its very short time of action (Duke Elder, Systems of OphtalmologyVolume XIII Part II p 634, 1974). Another disadvantage of most tear substitutes is that they contain benzalkonium, which has a damaging impact on eyes of mammals (Pjister, R. R. and Burstein, N., Invest Ophtalmol. 15:246, 1976). Also, many pharmaceutical formulations are very poorly adapted to the natural specific composition or electrolytic status of natural tear fluid (Gilbard, J. P., Rossi, S. R. and Heyda, K. G., American J of ophtalmology 107:348–355, 1989).

Carbachol chloride is a well-known substance in the treatment of glaucoma. For this indication its ability of lowering intraocular pressure is employed. Here, carbachol chloride is normally used in a concentration of 3% and in combination with benzalkonium chloride in order to obtain good penetration of the eye (Smolen, V. F., Clevenger, J. M., Williams, E. J. and Bergdolt, M. W., J of Pharmaceutical Sciences, 1973, 62 p 958). Other than having this effect, benzalKonium chloride in pharmaceutical mixtures has a preservative function. Other effects of carbachol chloride exposure to the eye are tear secretion, miosis and influence on the accomodatory ability of the eye. These so called cholinergic effects are in this context considered as side effects.

Substances having the same effects as carbachol chloride are methacholine chloride, methanecholine bromide, bethanechol chloride, furtrethonium iodide and arecoline.

Tear production can be stimulated also by other cholinergic substances such as acetylcholine, pilocarpine, physostigmine, neostigmine and others. These compounds, however, easily penetrate the cornea upon exposure, thereby activating cholinergically innervated intraocular structures such as the pupillary sphincter and the accomodation muscle, both unwanted side effects in cases where only extraocular effects are wanted. Such compounds, therefore, are less suited for this purpose than is carbachol.

DISCLOSURE OF THE INVENTION

The present invention concerns a novel pharmaceutical preparation containing cholinergic substances based on carbachol, methacholine, bethanechol, furtrethonium or arecoline, especially carbachol chloride, methanecholine chloride, methacholine bromide, bethanechol chloride, furtrethonium iodide and arecoline as active agent for the treatment of KCS and the use of carbachol for treatment of this disease. These substances actively stimulate the secretion of tears in mammals including man, resulting in a longer duration of the effect than is usually the case with medicaments not containing this type of component. For carbachol chloride the frequency of application can be kept as low as 3–4 times per day as compared to twice per hour with no carbachol present.

Carbachol chloride, methacholine chloride, methacholine bromide, bethanechol chloride, furtrethonium iodide and arecoline without addition of benzalkonium chloride have very little effect on the intraocular pressure but stimulate glands outside the eye to increased tear secretion. In low doses i.e. low concentrations no other effect than tear secretion can be observed. The present invention makes use of this property of these substances in that low concentrations are used for the purpose.

For the treatment of KCS in mammals, including man, an effective amount ranging from 5 µg to 600 µg of any of the above-mentioned cholinergic compounds is administered to a host in need of such treatment.

Patients treated with eye drops containing carbachol according to the invention have experienced a strong relief in their symptoms in that their eyes feel less irritated than after using other preparations. Also, the effect of treatment is longer. Of 52 treated patients only 6 have had no effect or side effects of the treatment.

METHODS OF PREPARATION

Solutions for application in the eye must, according to hygienic requirements be sterile. Sterility is also required in order to protect solutions containing carbachol from decomposing. Preservatives must not be added since they can cause damage to the eye. Concentrations of carbachol should preferably be between 0.01–1 percent by weight. The solution should be made isotonic or hypotonic. Additives of polymeric substances such as hypromellose, metyl cellulose, polyvinyl alcohol or hyaluronic acid could prolong the effect of carbachol.

METHODS OF PHARMACEUTICAL PREPARATION

Solutions for use as eyedrops are preferentially prepared by first aseptically mixing of all the necessary ingredients i.e. the active substance, salts and lubricant. If necessary the pH is adjusted to 5–7 using solutions of NaOH, KOH, HCl or boric acid. The solution is then sterilisedby autoclaving or sterile filtration and filled on one dose packings.

Solutions could also be preparedby first preparing solutions of each of the ingredients and then sterilising these solutions in the same manner as above before finally mixing and filling the solutions on one dose packings under aseptical conditions.

Examples of Pharmaceutical Formulations

| | |
|---|---|
| Carbachol chloride | 0.01–1.0 g |
| Sodium chloride | 0.5–0.09 g |
| Water for injection | ad 100 g |
| Carbachol chloride | 0.01–1.0 g |
| Boric acid | 1.15–3.0 g |
| Water for injection | ad 100 g |
| Carbachol chloride | 0.01–1.0 g |
| Polyvinyl alcohol | 1.4 g |
| Sodium chloride | 0.5–0.9 g |
| Water for injection | ad 100 g |
| Carbachol chloride | 0.01–1.0 g |
| Methyl cellulose | 0.5–1.0 g |
| Sodium chloride | 0.5–0.9 g |
| Water for injection | ad 100 g |
| Carbachol chloride | 0.01–1.0 g |
| Polyvinyl alcohol | 1.4 g |
| Sodium chloride | 0.45 g |
| Potassium chloride | 0.37 g |
| Water for injection | ad 100 g |

The eyedrops according to the formulations suggested can be applied directly to the eye either upon need or 3–4 times daily.

I claim:

1. A method for the topical treatment of dry eyes disease or KCS in human and other mammals comprising administering to a host in need of such treatment a therapeutically effective dosage of a pharmaceutical composition comprising as active ingredient about 0.01 to 1% by weight of a compound selected from the group consisting of carbachol, methacholine, bethanechol, furthrethonium and arecoline; and a pharmaceutically acceptable carrier.

2. The method according to claim 1 wherein the therapeutically effective dosage is about 5 µg to about 600 µg per application.

3. The method according to claim 1, wherein the pharmaceutically acceptable carrier is an isotonic or a hypotonic salt solution.

4. The method according to claim 1, wherein the pharmaceutical composition further comprises a pharmaceutically acceptable polymer.

5. The method according to claim 4, wherein the polymer is selected from the group consisting of hypromellose, methyl cellulose, polyvinyl alcohol, and hyaluronic acid.

6. The method according to claim 1, wherein the active ingredient selected from the group consisting of carbachol chloride, methanecholine chloride, methanecholine bromide, bethanechol chloride and furthrethonium iodide.

7. The method according to claim 1, wherein the active ingredient is carbachol chloride dissolved in an isotonic or hypotonic salt solution, and wherein the composition comprises a pharmaceutically acceptable polymer.

8. The method according to claim 3 or 4 wherein the salt solution has a pH range from 5–7.

9. The method according to claim 3 or 4 wherein the solution is sterile and devoid of preservatives.

10. The method according to claim 3 or 4 wherein the solution is suitable for application as eye drops.

\* \* \* \* \*